United States Patent [19]

Oráa, deceased et al.

[11] Patent Number: 4,665,096

[45] Date of Patent: May 12, 1987

[54] CONTRACEPTIVE METHODS AND COMPOSITIONS

[76] Inventors: Espartaco Oráa, deceased, late of Caracas, Venezuela, by Maritza Oráa de Cova, legal representative; by Maritza Oráa de Cova, legal representative, Calle Boyaca "Villa Pura" No. 3, El Rosal, Chacao, Caracas, Venezuela

[21] Appl. No.: 754,027

[22] Filed: Jul. 11, 1985

[51] Int. Cl.⁴ .............................................. A61K 31/19
[52] U.S. Cl. .................................... 514/557; 514/574; 514/843
[58] Field of Search .......................... 514/557, 574, 843

[56] References Cited

U.S. PATENT DOCUMENTS 2,752,284  6/1956  Berliner et al. ................. 514/843 X

OTHER PUBLICATIONS

Chemical Contraceptive, Bennett, J. P., pp. 10–11, Columbia University Press, 1974.
Laboratory Manual for the Examination of Human Semen and Semen–Cervical Mucus Interaction, Press Concern, Singapore, pp. 7–13, World Health Organization, 1980.
The Pharmacological Basis of Therapeutics, Goodman & Gilman, translated from English to Spanish by Jose Giral Pereira, pp. 752–754 and 937, Mexico City, 1945.

*Primary Examiner*—Leonard Schenkman
*Attorney, Agent, or Firm*—Karl F. Ross; Herbert Dubno

[57]  ABSTRACT

Postcoital contraception is carried out by the intravaginal administration of an aqueous solution of 2-hydroxy-propanoic acid, 3-hydroxy-3-carboxy-pentanodioic acid and acetic acid.

5 Claims, No Drawings

CONTRACEPTIVE METHODS AND COMPOSITIONS

FIELD OF THE INVENTION

My present invention relates to a contraceptive method, composition and device and, more particularly, to a contraceptive composition which, when applied intravaginally immediately after coitus, is significantly more effective than many of the contraceptive methods widely in use today and which can, because of the comparative low cost of its ingredients, be made available practically anywhere in the world at a relatively low cost, but nevertheless with high efficiency.

BACKGROUND OF THE INVENTION

There are a wide variety of contraceptive agents on the market and in general use, some of which require post-coital introduction into the vagina and can be considered spermaticides, working by effectively destroying the sperm in the vagina before they pass the cervix and create the possibility of fertilization of an ovum.

Various jellies or other compositions have been used for this purpose and other contraceptive methods such as the intrauterine device, which frequently causes irritation and discharge from the uterus, the diaphragm which is often uncomfortable, and the oral contraceptive which may be hormonally based and hence undesirable, have all been used with varying degrees of success, with greater or lesser amounts of discomfort, and at greater or lesser cost per application.

In spite of the fact that family planning is becoming increasingly more important as the world population grows and the drain on natural resources increases, and in spite of the fact that considerable research effort has been expended on various contraceptive techniques and operations, there has been, to my knowledge, no truly effective low-cost post-coitally applicable contraceptive method or composition which is substantially free of discomfort and yet virtually assures total destruction of the sperm following coitus.

OBJECTS OF THE INVENTION

It is, therefore, the principal object of the present invention to provide an improved post-coital method of contraception which utilizes a comparatively low-cost composition consisting entirely of constituents which are safe for any user, and which nevertheless is substantially one hundred percent effective in preventing fertilization of an ovum.

Another object of this invention is to provide an improved contraceptive composition which obviates the disadvantages of earlier contraceptive compositions and which has been used without the pronounced disadvantages of mechanical contraceptive techniques.

Yet another object of my invention is to provide a device for administering the composition in the improved contraceptive method of the present invention.

SUMMARY OF THE INVENTION

These objects and others, which will become apparent hereinafter, are attained in accordance with the present invention which comprises a method of contraception whereby, following coitus and preferably immediately after coitus, i.e. no more than 5 minutes after coitus, the vagina is irrigated with an aqueous solution of an effective amount of 2-hydroxy-propanoic acid

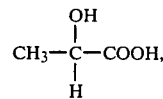

an effective amount of 3-hydroxy-3-carboxy-pentanedioic acid

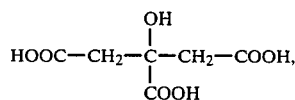

and an effective amount of acetic acid $CH_3COOH$ in a synergistic combination and preferably with the concentration of 2-hydroxy-propanoic acid being about 1.2 ml per 100 cc of the solution, the concentration of the 3-hydroxy-3-carboxy-pentanedioic acid being 0.9 ml per 100 cc of the solution and the acetic acid concentration being equivalent to 0.5 ml of glacial acetic acid per 100 cc of the solution. Water makes up the balance of the solution and for a scent, about 4 cc of the water may be constituted by rose water.

The solution is adjusted to a pH of 3.2 to 3.5 with 10 N sodium hydroxide (NaOH). The proportions of the active ingredients, namely the 2-hydroxy-propanoic acid, the 3-hydroxy-3-carboxy-pentanedioic acid and the acetic acid preferably are precisely as given above although deviations of ±10% can be used.

The composition can be fabricated simply by mixing the components together and adding the sodium hydroxide to bring about the pH up to the level indicated.

Surprisingly, while each or some of the active ingredients have been used as spermaticides in the past, for the concentrations given, none is totally effective and indeed no combination of two of them is totally effective, thereby indicating that all three components, when taken together, manifest a synergistic effect.

Interestingly enough, and equally surprising, is the fact that the 2-hydroxy-propanoic acid is a naturally occuring substance present in the vagina, having a protective effect against vaginal infections and is formed in the vagina apparently by fermentation of the glucose by the Doderlein bacillus.

The 3-hydroxy-3-carboxy-pentanedioic acid, likewise, is a naturally occurring bodily substance and, quite surprisingly, is found in the male genital tract and appears to have the function of liquefying semen once it has been ejaculated.

The acetic acid, of course, is a compound produced in normal metabolism. Thus all of the active ingredients are present as naturally occurring compounds in the body. That, presumably, is why the compound can be utilized without adverse effects repeatedly and with total effectiveness.

According to another aspect of the invention, the composition is administered by a vaginal irrigator characterized by the fact that it has an elongated tube which can be inserted into the vagina and is formed remote from its discharge end with a disk which temporarily presses on the tissue surrounding the mouth of the vagina and blocks escape of the solution which is injected through this device into the vagina.

Generally speaking, 8 to 10 $cm^3$ of the contraceptive solution is sufficient to fill and encompass the complete vaginal space, although slightly more of the solution, up to, say, 12 cc may be used if the vagina has been distended owing to childbirth.

The disk is preferably oval to fit effectively against the tissue surrounding the mouth of the vagina.

A surprising characteristic of the composition, demonstrated by tests in vitro and in vivo is that the composition does not change in character when it is mixed with vaginal discharge. The composition is effective, regardless of the quantity of spermatozoa, all sperm are destroyed.

SPECIFIC EXAMPLE

A composition 1 is prepared by mixing 1.2 ml of 2 hydroxy propanoic acid, 0.9 ml of 3 hydroxy-3-carboxy pentanodioic acid, 0.5 ml of acetic acid (glacial), 4 ml of rose water, and distilled water to bring the solution to 100 ml. Drop by drop, 10 N sodium hydroxy is added at a pH of 3.2 to 3.5.

Immediately after coitus, 10 ml of this solution are administered using the device and held in the vagina for a period of 2 to 3 minutes. Smears show no surviving sperm.

Tests were carried out on over 1000 in vivo specimens under the microscope using human fresh semen and in all cases administration of solution killed all spermatozoa.

242 couples voluntarily submitted to tests, the semen having been contributed by the male partner and the female partners having been tested previously to be certain that they were not pregnant. All tests and examinations were carried out in my laboratory and outpatient clinic.

Once it was proven without a doubt that the woman were not pregnant, during their ovulation period, the semen of the respective male partner was introduced and, in the manner described above, the contraceptive solution was applied.

25 to 35 days later all were given approved pregnancy slide tests and none of the test subjects was pregnant. There were no side effects.

The solution was used voluntarily by 28 women between 18 and 30 years of age for more than 26 consecutive days and retained in the vagina for 10 minutes on each application.

No secondary effects were observed.

The solution does not appear to lose its effectiveness or deteriorate at ambient temperature and does not need refrigeration. It is transparent and no sedimentation is observed. The solution does not stain clothing or the skin, and is not affected by vaginal flow. I observed no allergic phenomenon or any other secondary effect and the only sensation which appears to be a concomittant of its use is a mildly freshening sensation upon application.

It is claimed:

1. A method of contraception which comprises postcoitally irrigating the vagina with an aqueous solution of substantially 1.2 ml per 100 cc of 2-hydroxy-propanoic acid, substantially 0.9 ml per 100 cc of 3-hydroxy-3-carboxy-pentanedioic acid and substantially 0.5 ml of glacial acetic acid per 100 cc, at a pH of substantially to 3.5, and retaining said solution in the vagina for a period sufficient to effect substantially complete spermatocidal action therein.

2. The method defined in claim 1 wherein the solution is retained in the vagina for up to 3 minutes.

3. The method defined in claim 1 wherein said solution is maintained in the vagina for at least 10 minutes.

4. The method defined in claim 1 wherein said solution is injected in an amount of substantially 8 to 12 cc into the vagina through an irrigator tube formed with an oval disk closing the mouth of the vagina.

5. A contraceptive composition consisting essentially of an aqueous solution containing substantially 1.2 ml per 100 cc of 2-hydroxy-propanoic acid, substantially 0.9 ml per 100 cc of 3-hydroxy-3-carboxy-pentanedioic acid, and substantially 0.5 ml of glacial acetic acid per 100 cc, said solution having a pH of 3.2 to 3.5.

* * * * *